(12) United States Patent
Shaw

(10) Patent No.: US 8,870,947 B2
(45) Date of Patent: Oct. 28, 2014

(54) MEDICAL DEVICE FIXATION ANCHORS

(75) Inventor: Edward E. Shaw, Flagstaff, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/615,325

(22) Filed: Sep. 13, 2012

(65) Prior Publication Data
US 2013/0073029 A1 Mar. 21, 2013

Related U.S. Application Data

(60) Provisional application No. 61/535,830, filed on Sep. 16, 2011.

(51) Int. Cl.
*A61F 2/06* (2013.01)
*A61B 17/12* (2006.01)
*A61B 17/00* (2006.01)
*A61F 2/848* (2013.01)
*A61F 2/86* (2013.01)

(52) U.S. Cl.
CPC ....... *A61F 2/848* (2013.01); *A61B 2017/00597* (2013.01); *A61B 2017/00592* (2013.01); *A61B 2017/00243* (2013.01); *A61F 2002/8483* (2013.01); *A61F 2/86* (2013.01); *A61B 2017/00867* (2013.01); *A61B 17/12122* (2013.01); *A61B 2017/00862* (2013.01); *A61B 2017/00632* (2013.01); *A61B 2017/00579* (2013.01)
USPC ...................................... 623/1.36

(58) Field of Classification Search
USPC ...................................... 623/1.36
See application file for complete search history.

(56) References Cited

U.S. PATENT DOCUMENTS

| 5,217,486 A | 6/1993 | Rice et al. |
| 5,344,427 A | 9/1994 | Cottenceau et al. |
| 5,562,726 A | 10/1996 | Chuter |

(Continued)

FOREIGN PATENT DOCUMENTS

| EP | 204810381 | 8/2012 |
| WO | WO 2005/072652 | 8/2005 |
| WO | WO 2010/024881 | 3/2010 |
| WO | WO 2011/031981 | 3/2011 |

OTHER PUBLICATIONS

International Search Report & Written Opinion, mailed Dec. 5, 2012, 15 pages.

(Continued)

*Primary Examiner* — David Isabella
*Assistant Examiner* — Dinah Baria
(74) *Attorney, Agent, or Firm* — Fish & Richardson P.C.

(57) ABSTRACT

An implantable medical device includes a frame that includes at least one elongate member. The implantable medical device also includes a fixation member that has a first cuff, a second cuff, a tissue engagement member configured to anchor to tissue at an implant site to thereby hold the implantable medical device in a position at the implant site, and a cuff joining member that has an arcuate shape and that is connected at a first end to the first cuff and at a second end to the second cuff. The first cuff substantially surrounds a perimeter of a first portion of the at least one elongate member, the second cuff substantially surrounds a perimeter of a second portion of the at least one elongate member, and the cuff joining member does not substantially surround a perimeter of any portion of the at least one elongate member.

24 Claims, 9 Drawing Sheets

(56) References Cited

U.S. PATENT DOCUMENTS

| | | | |
|---|---|---|---|
| 5,709,704 | A | 1/1998 | Nott et al. |
| 5,713,917 | A | 2/1998 | Leonhardt et al. |
| 5,720,776 | A | 2/1998 | Chuter et al. |
| 5,904,703 | A | 5/1999 | Gilson |
| 5,961,546 | A * | 10/1999 | Robinson et al. ............ 623/1.14 |
| 6,013,093 | A | 1/2000 | Nott et al. |
| 6,214,025 | B1 | 4/2001 | Thistle et al. |
| 6,231,581 | B1 | 5/2001 | Shank et al. |
| 6,231,589 | B1 | 5/2001 | Wessman et al. |
| 6,273,900 | B1 | 8/2001 | Nott et al. |
| 6,322,585 | B1 | 11/2001 | Khosravi et al. |
| 6,328,727 | B1 | 12/2001 | Frazier et al. |
| 6,451,051 | B2 | 9/2002 | Drasler et al. |
| 6,485,513 | B1 | 11/2002 | Fan |
| 6,491,704 | B2 | 12/2002 | Gifford, III et al. |
| 6,712,842 | B1 | 3/2004 | Gifford, III et al. |
| 6,746,472 | B2 | 6/2004 | Frazier et al. |
| 7,169,160 | B1 | 1/2007 | Middleman et al. |
| 7,331,992 | B2 | 2/2008 | Randall et al. |
| 7,572,289 | B2 | 8/2009 | Sisken et al. |
| 7,601,159 | B2 | 10/2009 | Ewers et al. |
| 7,655,034 | B2 | 2/2010 | Mitchell et al. |
| 7,815,591 | B2 | 10/2010 | Levine et al. |
| 7,846,179 | B2 | 12/2010 | Belef et al. |
| 7,887,580 | B2 | 2/2011 | Randall et al. |
| 8,029,559 | B2 | 10/2011 | Sisken et al. |
| 8,241,350 | B2 | 8/2012 | Randall et al. |
| 8,273,105 | B2 | 9/2012 | Cohen et al. |
| 2004/0034366 | A1 | 2/2004 | Van der Burg et al. |
| 2008/0147111 | A1 | 6/2008 | Johnson et al. |
| 2008/0208329 | A1 | 8/2008 | Bishop |
| 2009/0054723 | A1 | 2/2009 | Khairkhahan et al. |
| 2009/0062838 | A1 | 3/2009 | Brumleve et al. |
| 2011/0054515 | A1 | 3/2011 | Bridgeman et al. |
| 2012/0022638 | A1 | 1/2012 | Leewood et al. |
| 2013/0023981 | A1 * | 1/2013 | Dierking et al. ............ 623/1.35 |
| 2013/0245666 | A1 | 9/2013 | Larsen et al. |

OTHER PUBLICATIONS

International Preliminary Report on Patentability for PCT/US2012/055537, issued Mar 18, 2014, 10 pages.

International Preliminary Report on Patentability for PCT/US2012/055445 issued Mar. 18, 2014, 9 pages.

International Search Report and Written Opinion for PCT/US2012/055537, mailed Dec. 5, 2012, 5 pages.

* cited by examiner

MEDICAL DEVICE FIXATION ANCHORS

CROSS-REFERENCE TO RELATED APPLICATIONS

This application claims priority to U.S. Provisional Application No. 61/535,830, filed Sep. 16, 2011. The disclosure of the prior application is considered part of (and is incorporated by reference in) the disclosure of this application.

TECHNICAL FIELD

This specification relates to fixation anchors that are useful, for example, for securing implantable medical devices in position within bodily cavities and vessels.

BACKGROUND

A wide variety of known medical devices can be implanted within a patient's body to provide interventional or remedial treatments. Occlusion devices, for example, can be implanted to close perforations in septa, conduits, or ostia. An atrial septal defect in the heart, which is an abnormal opening in the septum between the left and right atria of the heart, is one such condition that can be treated by implanting an occlusion device to close the abnormal opening. Stent grafts provide another example of a class of implantable medical devices. A stent graft can be a generally tubular device, typically constructed of fabric that is mechanically supported by a relatively rigid structural framework called a stent frame. Stent grafts are often used to treat weak points, known as aneurisms, in the vasculature of a patient. For example, an abdominal aortic aneurism ("AAA") is a localized dilation of the wall of the aorta in the abdominal region. A stent graft can be used to treat an AAA condition by being deployed within the aorta to act as a lining that traverses the aneurism; to reduce the stress on the aneurism caused by normal blood pressure and flow by permitting blood flow to bypass the aneurism, which may prevent a potentially deadly rupture of the aneurism. Many other types of known medical devices can be also implanted in patients to treat a wide variety of maladies.

Once deployed to the desired position within a patient, the ongoing efficacy of implantable devices can often depend on their ability to remain in an approximately fixed position relative to the surrounding tissue. For example, an occlusion device implanted to occlude or close an aperture should maintain its proper position relative to the tissue surrounding the aperture, or it may fail to close the aperture. Similarly, an AAA stent graft implanted to relieve stress on an aneurism should maintain its proper position as a lining within the aorta to traverse the AAA.

Fixation anchors or hooks can help perform the important function of securing an implantable medical device to the surrounding tissue and maintaining the device in proper position. In some cases, other parts of the device, such as a stent frame, can supply a force that presses the fixation anchors into contact with the tissue. Often, a fixation anchor includes a relatively sharp point like an arrow or a hook that is designed to penetrate the tissue. In some cases, a fixation anchor does not include a sharp point, and is intended to contact the tissue without penetrating it.

Currently, an increasing number of implantable medical devices are deployed using minimally invasive techniques. In such cases, the medical device is typically configured in a collapsed arrangement and delivered to the internal deployment site via a delivery catheter or sheath. At the deployment site, the medical device is ejected from the catheter and it expands to a larger size to effectively treat the particular medical condition. In many cases the minimally invasive delivery techniques require the medical device to be constructed from a frame that is resilient and compliant enough to be compressed into the lumen of a delivery catheter without causing permanent deformation to the device. When fixation anchors are included as an integral part of an implantable medical device, the fixation anchors must collapse with the frame to fit within the lumen of a delivery catheter.

SUMMARY

This specification describes fixation anchors for use with implantable medical devices. The fixation anchors can be used with a wide variety of implantable medical devices for implantation at various locations within a patient's body. The fixation anchors may prevent migration of the implantable medical devices following implantation, and may facilitate stable and consistent location and positioning within the patient's body. The fixation anchors described herein can be engaged with an elongate frame member of an implantable medical device, such as an elongate member of a stent frame or an elongate member of an occlusion device. Further, the fixation anchors can be advantageously engaged with the elongate frame member of an implantable medical device at a location of a bend in the elongate frame member.

In a first general aspect, an implantable medical device includes a frame that includes at least one elongate member. The implantable medical device also includes a fixation member comprising a first cuff, a second cuff, a tissue engagement member configured to anchor to tissue at an implant site to thereby hold the implantable medical device in a position at the implant site, and a cuff joining member comprising an arcuate shape and connected at a first end to the first cuff and at a second end to the second cuff. The first cuff substantially surrounds a perimeter of a first portion of the at least one elongate member, the second cuff substantially surrounds a perimeter of a second portion of the at least one elongate member, and the cuff joining member does not substantially surround a perimeter of any portion of the at least one elongate member.

In various implementations, the tissue engagement member may be configured to penetrate the tissue at the implant site. The tissue engagement member may be configured to contact, without penetrating, the tissue at the implant site. The tissue engagement member may extend from the first cuff. The implantable medical device may further include a second tissue engagement member that may extend from the second cuff. The tissue engagement member may extend from the second cuff. The tissue engagement member may extend from the cuff joining member. The first cuff and the second cuff may each have a slip-fit relation to the at least one elongate member. The first cuff and the second cuff may be respectively positioned on opposite sides of a bend portion of the at least one elongate member. The cuff joining member may be biased to follow an inside curvature of the bend portion of the at least one elongate member. The first cuff may be fixedly attached to the at least one elongate member. The first cuff may be fixedly attached to the at least one elongate member one of crimping, welding, or gluing. The second cuff may be fixedly attached to the at least one elongate member. The second cuff may have a slip-fit relation to the at least one elongate member. The first cuff may define a first lumen through the first cuff, the second cuff may define a second lumen through the second cuff, and a first axis coincident with the first lumen may not be collinear with a second axis coincident with the second lumen. The first axis and the second axis may intersect at an angle in the range of 10-80 degrees. The first axis and the second axis may intersect at an angle in the range of 20-70 degrees. The first axis and the second axis may intersect at an angle in the range of 30-60 degrees. The at least one elongate member may include a wire. The wire may include nitinol. The fixation member may include a nitinol tube from which the first cuff, the second cuff, the cuff joining member, and the tissue engagement member are formed. The first cuff may include a generally linear gap along an axial direction of a wall of the first cuff. The first cuff may completely surround the perimeter of the first portion of the at least one elongate member.

In a second general aspect, an implantable medical device includes a frame that includes at least one elongate member. The implantable medical device also includes a fixation member that includes a first cuff, a second cuff, a tissue engagement member configured to anchor to tissue at an implant site to thereby hold the implantable medical device in a position at the implant site, and an elongate joining member comprising a proximal end and a distal end, where the elongate joining member is connected at the proximal end to the first cuff and at the distal end to the second cuff, and where the elongate joining member further defines an arcuate shape between the proximal end and the distal end. The first cuff substantially surrounds a perimeter of a first portion of the at least one elongate member, the second cuff substantially surrounds a perimeter of a second portion of the at least one elongate member, and the elongate joining member does not substantially surround a perimeter of any portion of the at least one elongate member.

In a third general aspect, an implantable medical device includes a frame comprising at least one elongate member. The implantable medical device also includes a fixation member that includes a first tubular member, a second tubular member, a tissue engagement member configured to anchor to tissue at an implant site to thereby hold the implantable medical device in a position at the implant site, and an elongate joining member comprising a proximal end and a distal end, the elongate joining member connected at the proximal end to the first tubular member and at the distal end to the second tubular member. The elongate joining member further defines an arcuate shape between the proximal end and the distal end. The first tubular member substantially circumferentially surrounds a first portion of the at least one elongate member, the second tubular member substantially circumferentially surrounds a second portion of the at least one elongate member, and the elongate joining member does not substantially circumferentially surround any portion of the at least one elongate member.

Particular embodiments of the subject matter described in this specification can be implemented so as to realize one or more of the following advantages. The fixation anchors provided herein can, in some cases, be efficiently fabricated from a single piece of tubing. The fixation anchors can, in some implementations, be readily properly positioned with respect to the implantable medical device, both laterally and radially, at the bend of an elongate member. One or both collars of the fixation anchors can have a slip fit with respect to the elongate member to allow for collapsing and expansion of the implantable medical device with minimal resistance from the fixation anchors. The fixation anchors can provide a low profile in their collapsed configuration to enable the use of a minimally sized deployment catheter. A single fixation anchor can have one or more anchoring members, and can be configured in multiple arrangements to compliment a wide variation of types of implantable medical devices and patient anatomies. An arcuate feature of a connecting or joining member of the fixation anchors can facilitate a bias to follow an inside curvature of an elongate member at a bend portion of an implantable medical device.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
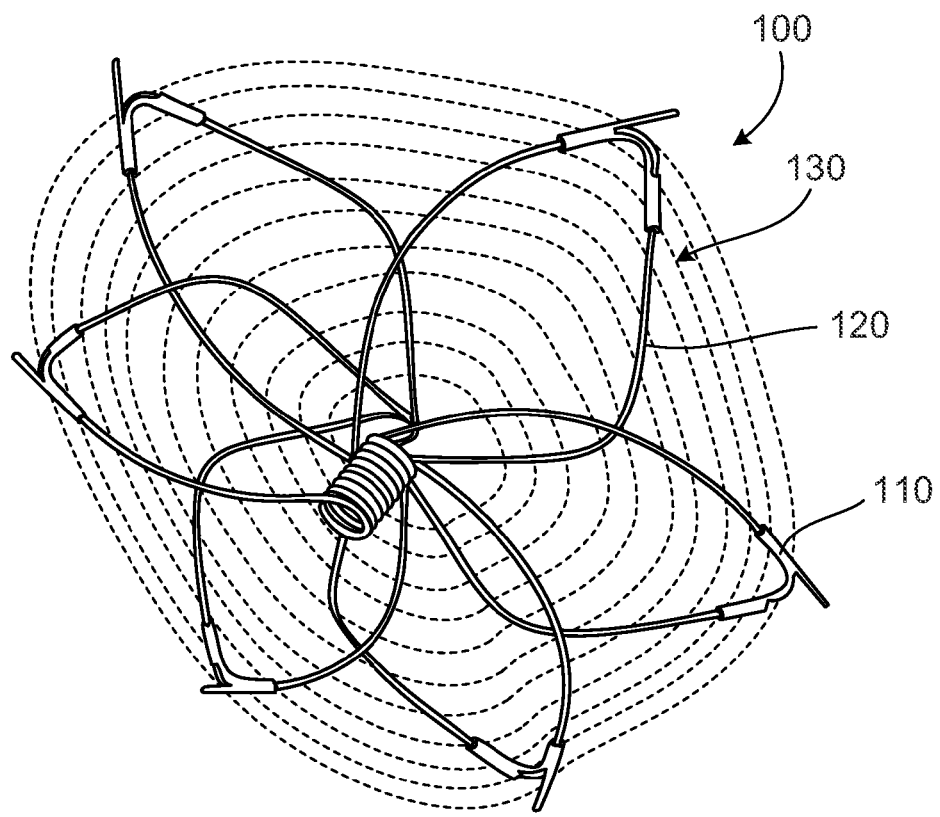
FIG. 1 is a perspective view of an example embodiment of an implantable medical device including example fixation anchors.

FIG. 1 illustrates an example implantable medical device that includes an example embodiment of the fixation anchors described herein. The implantable medical device illustrated is an example occluder device 100 that can be used to occlude a structure or a conduit, such as a left atrial appendage or other aperture within the body. The example occluder device 100 is an illustrative embodiment of a type of implantable medical device that can utilize the fixation anchors described herein. Further non-limiting examples will be provided below, and many other beneficial applications for the fixation anchors provided herein, in conjunction with other types of devices (e.g., vascular occluders, patent ductus arteriosus ("PDA") occluders, AAA stent graft devices, and others) are envisioned.

The example occluder device 100 generally includes fixation anchors 110, frame members 120, and occlusive membrane 130. The occlusive membrane 130 is drawn in phantom lines so that the fixation anchors 110 and frame members 120 are visible. In some implementations, the occlusive membrane 130 covers at least a portion of the frame of the device, for example. As used herein, "frame" may refer to an entire frame of a device, or may alternatively refer to a localized portion of a device that includes at least one elongate member.

FIG. 1 depicts the example occluder device 100 in its deployed configuration. The example occluder device 100 can be designed for minimally invasive implantation. To install the example occluder device 100 in a minimally invasive manner, a delivery catheter or sheath (not shown) can be used. The example occluder device 100, including the fixation anchors 110, can be stretched, elongated, or folded to a low profile for containment within a lumen of the delivery catheter, and can be advanced through the lumen of the delivery catheter to a delivery site. When the example occluder device 100 is deployed from the lumen of the delivery catheter, the example occluder device 100 can self-expand to a deployed configuration, approximately as shown in FIG. 1. In some examples, the example occluder device 100 is configured to flexibly conform to the shape of the aperture at which it is deployed.

In some implementations, the occluder device 100 may self-expand as a result of the bias of the frame members 120. The frame members 120 can be, for example, spring wires, shape memory alloy wires, or super-elastic alloy wires. The frame members 120 can be made of nitinol (NiTi), L605 steel, stainless steel, or any other appropriate biocompatible material. The super-elastic properties of NiTi make it a particularly good candidate material for such frame members 120 (e.g., NiTi wires can be heat-set into a desired shape). The frame members 120 may include one or more bend regions that can provide, for example, suitable positions for anchoring features, such as the fixation anchors provided herein.

The occlusive membrane 130 can be configured to inhibit passage of blood and other bodily fluids. In some embodiments, the occlusive membrane 130 can have a microporous structure that provides a tissue ingrowth scaffold for durable occlusion and supplemental anchoring strength of the example occlusive device 100. Some embodiments of the occlusive membrane 130 comprise a fluoropolymer, such as an expanded polytetrafluoroethylene (ePTFE) polymer.

The example occlusive device 100 can also include one or more fixation anchors 110 disposed on one or more regions of the frame members 120. When the example occluder device 100 is in the deployed configuration, as shown in FIG. 1, the fixation anchors 110 can be generally disposed at positions around the periphery of the occlusive membrane 130, and at the locations of the bends of the frame members 120. At those positions, the fixation anchors 110 can make contact with the tissue in proximity to the aperture to be occluded. In various implementations, the fixation anchors 110 may be adapted to contact, engage, or puncture the tissue at the delivery site in order to anchor the example occlusive device 100 to the delivery site. The occlusive membrane 130 can include holes that allow the fixation anchors 110 to pass through the occlusive membrane 130, or the fixation anchors 110 can simply puncture through the occlusive membrane 130 in some implementations. In some embodiments, the self-expanding nature of the frame members 120 can provide a radial force to cause the fixation anchors 110 to contact, engage, or puncture the tissue at the delivery site as needed. In some embodiments, a supplemental force can be applied—for example, a temporary supplemental force from a balloon device, post-deployment—to assist with the tissue contact, engagement, or puncture by the fixation anchors 110.

The fixation anchors 110, and in particular a tissue engagement portion of the fixation anchors, may extend from the frame members 120 at various angles (e.g., at an acute angle, at a right angle, or at an obtuse angle) and in various directions. In some examples, the fixation anchors 110 may extend tangentially from the periphery of the example occluder device 100. In some examples, the fixation anchors 110 may extend in a lateral or partially lateral direction from the face of the example occluder device 100. In some examples, the fixation anchors 110 may extend from the frame members 120 in a generally clockwise direction as shown. In other examples, the fixation anchors 110 may extend from the frame members 120 in a generally counterclockwise direction. In other examples, the fixation anchors 110 may extend from the example occluder device 100 in a substantially radial direction. Combinations of the foregoing are also possible. In some implementations, all of the fixation anchors 110 may be commonly oriented. In some implementations, a first set of one or more fixation anchors may be oriented according to a first orientation, and a second set of one or more fixation anchors may be oriented according to a second orientation.

The fixation anchors 110 can be made from a variety of suitable materials. For example, the fixation anchors 110 can be made of NiTi, L605 steel, stainless steel, a polymeric material, or any other appropriate biocompatible material. In some embodiments, the fixation anchors 110 can be made from a non-permanent biodegradable or bioabsorbable material.

The super-elastic properties of NiTi make it a particularly good candidate material for such fixation anchors 110. For example, the super-elasticity of NiTi can allow a fixation anchor 110 of NiTi to be flexed to a low profile for containment within a delivery catheter or sheath. Further, NiTi can be heat set so that a fixation anchor 110 can self-expand into a desired shape when the fixation anchor is placed in a less restrictive environment, such as when it is deployed from the delivery catheter to a body cavity. In some embodiments, as will be described further below, it is desirable for a fixation anchor 110 to be biased to have a particular shape to enhance the anchoring properties of the fixation anchor 110.

The fixation anchors 110 can, in some cases, be fabricated from tubing material (e.g., NiTi tubes or stainless steel tubes), including precision tubing material. The tubing can, in some examples, be laser cut to the desired configuration. Laser cutting can facilitate the fabrication of fixation anchors 110 in relatively complex shapes and with precision tolerances. In some examples, electrical discharge machining or turning can also be used for fabricating the fixation anchors 110.

The fixation anchors 110 can be fabricated from tubing to provide attachment features that facilitate placement or location, including maintaining a placement location, of the fixation anchors 110 at a desired location on a host medical device (e.g., at desired locations on the frame members 120 of example occluder device 100). For example, one or more portions of the fixation anchors can include a tube section to surround a frame member of a device. In some examples, an inner diameter of the tube section can be slightly larger than the frame member to provide a slip fit. In other examples, the tube section can have an interference fit, or be crimped-to or otherwise fixedly attached to the frame member.

For additional information regarding examples of medical devices that the anchors disclosed herein can be used with, and for example discussions regarding making the devices, see co-pending U.S. patent application titled, "Occlusive Devices," filed 13 Sep. 2012, with Coby C. Larsen, Steven J. Masters, and Edward E. Shaw as inventors, the entire contents of which are hereby incorporated by reference for all purposes.

Figure 2:
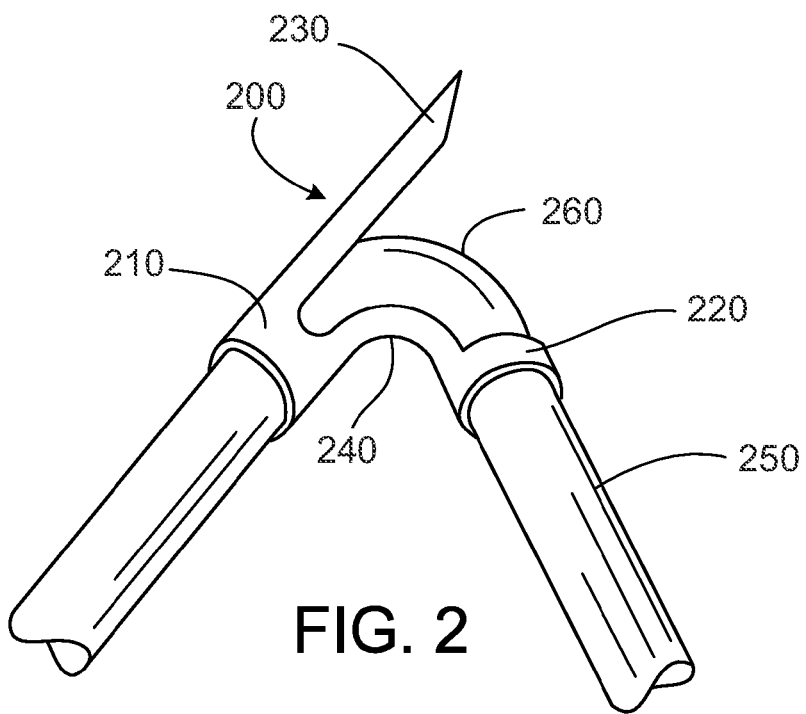
FIG. 2 is a perspective view of an example embodiment of a fixation anchor.

FIG. 2 illustrates an example embodiment of a fixation anchor 200. The fixation anchor 200 can be engaged or located on a frame member 250 as shown. The frame member 250 can be, for example, a portion of a frame comprised of elongate members, such as the frame members 120 of the example occluder device 100, or, more generally, of any host medical device. In some examples, the frame member is a NiTi wire. The frame member 250 can have a round cross-section, or various other shapes as well. For example, in some embodiments, the frame member 250 may have an oval, square, rectangle, diamond, triangle, or other polygonal cross-sectional shape. The frame member 250 can include a bend portion 260. The bend portion 260 can have any appropriate bend angle (e.g., an acute angle, a right angle, or an obtuse angle). The bend portion 260 in FIG. 2 includes an acute angle (that is, an angle less than 90 degrees) of about 60 degrees.

In some implementations, the fixation anchor 200 can generally include a first cuff 210, a second cuff 220, one or more tissue engagement members 230, and a cuff joining member 240. The first and second cuffs 210/220 can be conjoined by the cuff joining member 240. The cuff joining member 240 may be a portion of the fixation anchor 200 that is disposed between the first cuff 210 and the second cuff 220, and connects the first cuff 210 with the second cuff 220. In some implementations, the cuff joining member 240 covers or surrounds the periphery of the frame member 250 by less than about 180 degrees. That is, of the 360 degree periphery of the frame member 250, less than about 180 degrees (e.g., about 170 degrees, about 150 degrees, about 130 degrees, about 110 degrees, about 90 degrees, about 70 degrees, about 50 degrees, or about 30 degrees) of the periphery of the frame member 250 may be covered or surrounded by the cuff joining member 240. Similarly, the cuff joining member 240 may cover or surround less than half (50%) of the periphery of the frame member 250 (e.g., about 45%, 40%, 35%, 30%, 25%, 20%, 15%, 10%, or 5%). The one or more tissue engagement members 230 can project from either or both cuffs or, in some embodiments, from the cuff joining member 240.

In some embodiments, the first and second cuffs 210/220 can each substantially surround the entire 360 degrees of the periphery of the frame member 250. In cases where the first and second cuffs 210/220 substantially surround the frame member 250, the assembly of the fixation anchor 200 onto the frame member 250 may be accomplished by threading or sliding the frame member 250 through the first and second cuffs 210/220 of the fixation anchor 200. Alternatively, and as will be described more below, in some cases one or both of the cuffs 210/220 can have one wall region that is cut in an axial direction. Cutting the cuffs 210/220 in an axial direction can facilitate the assembly of the fixation anchor 200 onto the frame member 250 by enabling the cuffs 210/220 to be temporarily deflected open to a U-shape so they can be placed over the frame member 250, and then allowed to naturally close around the frame member 250. In this manner, the process of threading the frame member 250 through the cuffs 210/220 may be avoided. In some embodiments, the first and second cuff members 210/220 can surround the frame member 250 from between 180 to 360 degrees of the periphery of the frame member 250. The first and second cuff members 210/220 may surround the frame member 250 in equal amounts or unequal amounts, respectively.

The first cuff defines a first lumen through the first cuff and through which the frame member 250 can pass, and the second cuff defines a second lumen through the second cuff, through which the frame member 250 can also pass. As can be seen with reference to FIG. 2, first axis coincident with the first lumen is not collinear with a second axis coincident with the second lumen. That is, axes respectively defined by the first cuff and the second cuff intersect at an angle other than 180 degrees. In some examples, the axis defined by the first cuff intersects the axis defined by the second cuff at an angle in the range of about 10-80 degrees, or in the range of about 20-70 degrees, or in the range of about 30-60 degrees. In some examples, the axes intersect at an angle of about 90 degrees.

The first and second cuffs 210/220 can be, in some cases, fixedly coupled to the frame member 250. Alternatively, the cuffs 210/220 can have a slip fit relationship with the frame member 250. In some embodiments, one cuff (either the first cuff 210 or the second cuff 220) can have a slip fit with the frame member 250, and the other cuff can be fixedly coupled to the frame member 250. In other embodiments, both the first and second cuffs 210/220 can have a slip fit arrangement with the frame member 250, or both cuffs 210/220 can be fixedly coupled to the frame member 250. When one or both cuffs 210/220 have a slip fit relationship with the frame member 250, the fixation anchor 200 may provide less resistance to being collapsed or folded to a low-profile arrangement for containment within a delivery catheter. This feature may enable the host medical device to be deployed using a small or minimally sized delivery catheter or sheath.

When one or both cuffs 210/220 are fixedly attached to the frame member 250, the attachment of the cuffs 210/220 to the frame member 250 can be accomplished in a variety of manners. For example, the inner diameter of the cuffs 210/220 can be slightly smaller than the diameter of the frame member 250, so that an interference fit is created to thereby fixedly attach the cuffs 210/220 to the frame member 250. In other embodiments, the cuffs 210/220 can be, for example, crimped, welded, glued, or otherwise adhesively attached to the frame member 250. When one or both cuffs 210/220 are fixedly attached to the frame member 250, the fixation anchor 200 may be effectively located and oriented with respect to the frame member 250. That is, the location of the fixation anchor 200, and the orientation of the tissue engagement member 230, with respect to the overall host medical device, can be established when one or both cuffs 210/220 are fixedly attached to the frame member 250.

In contrast to fixedly attaching the cuffs 210/220 to the frame member 250, in some embodiments advantages can be realized when both cuffs 210/220 have a slip-fit relation to the frame member 250. In those cases, the bend portion 260 of the frame member 250 and properties of the fixation anchor 200 can induce the fixation anchor 200 to assume the desired location and orientation with respect to the overall host medical device, according to some implementations. For example, the first and second cuffs 210/220 can be positioned on opposite sides of the bend portion 260, as shown in FIG. 2. Because, in a slip-fit relationship, the inner diameters of the cuffs 210/220 may be only slightly larger than the diameter of the frame member 250, and because the cuffs 210/220 may be generally linear portions, each of the cuffs 210/220 may be restrained from migrating onto the bend portion 260. That is, even though each cuff may have a slip fit relationship with the frame member 250, because the cuffs are located on opposite sides of the bend portion and because the cuffs are generally linear, the cuffs 210/220 may be restrained from migrating from their home positions on each side of the bend portion 260. In this manner, the axial location of the fixation anchor 200 can be established and maintained in relation to the overall host medical device.

The bend portion 260, in combination with the cuff joining member 240 of the fixation anchor 200, can also facilitate establishing and maintaining a desired radial orientation of the fixation anchor 200, and more particularly a desired radial orientation of the tissue engagement member 230. For example, when the frame member 250 is bent such that the first cuff 210 and second cuff 220 are positioned on opposite sides of the bend portion 260, in some embodiments the cuff joining member 240 may naturally seek or be biased to a position at the inner radius of the bend portion 260, where the cuff joining member 240 can maintain its shortest length. That is, the cuff-joining member may be biased to follow or align with the inside curvature of the frame member 250. The cuff joining member 240 may resist being stretched, for example, and, if allowed, may naturally move into a position to avoid being stretched, and may thereby rotate the entire fixation anchor 200 on the axis of the frame member 250. In some cases, the cuff joining member 240 will therefore seek a position at the inner bend radius of the bend portion 260 to avoid being stretched. In this manner, the radial orientation of the fixation member 200 can be established in relation to the frame member 250, and in relation to the overall host medical device. The cuff joining member 240 may be flexible enough to follow the profile of the frame member 250. The cuff joining member 240 may have an arcuate shape approximately corresponding to the arcuate shape of the bend portion 260.

In some embodiments, the fixation anchor 200 can include two or more cuff joining members 240 (not shown in FIG. 2). In an example anchor embodiment that includes two or more cuff joining members 240, the cuff joining members 240 can have approximately equal lengths. This embodiment can also serve to establish a desired radial orientation of the fixation anchor 200. For example, when the cuffs 210/220 are on opposite sides of the bend portion 260 (spaced 180 degree apart from each other), the two cuff joining members 240 of equal lengths will each naturally resist being stretched and/or compressed. As such, the two cuff joining members 240 may seek home positions on opposite sides of the bend portion 260, but not at the inner or outer bend radii of the bend portion 260. This arrangement of two cuff joining members 240 in relation to the bend portion 260 can be visualized as being analogous, in a general sense, to the structure of the medial collateral and lateral collateral ligaments in relation to a human's knee.

The one or more tissue engagement members 230 can extend away from the frame member 250 to contact surrounding tissue in a variety of manners. Generally, the type of the host medical device, and the context of its use, will determine the desirable configuration(s) of the tissue engagement members 230. For example, as shown in FIG. 2, the tissue engagement members 230 can extend outwardly from the frame member 250, and approximately in a plane defined by the frame member 250.

Referring back now to the broader illustration provided by the example occluder device 100 of FIG. 1, the tissue engagement members can be seen to extend radially from the plane defined by the face of the occlusive membrane 130. Such a configuration may be generally desirable for an occlusion device, in particular because of the orientation of the device in relation to the tissue surrounding an aperture to be closed by the example occluder device 100. For example, it can be seen in FIG. 1 that the anchors are positioned generally at or near the apices or tips of the "petals" that form an occlusive face of the device 100. This, in combination with the tissue engagement member orientation of the anchors may facilitate anchoring in the ostium of the left atrial appendage ("LAA"), which may be a desirable anchoring point for LAA occlusion applications. As will be explained next, other types of medical devices may benefit from a different orientation of the tissue engagement members 230 in relation to the medical device.

Figure 3:
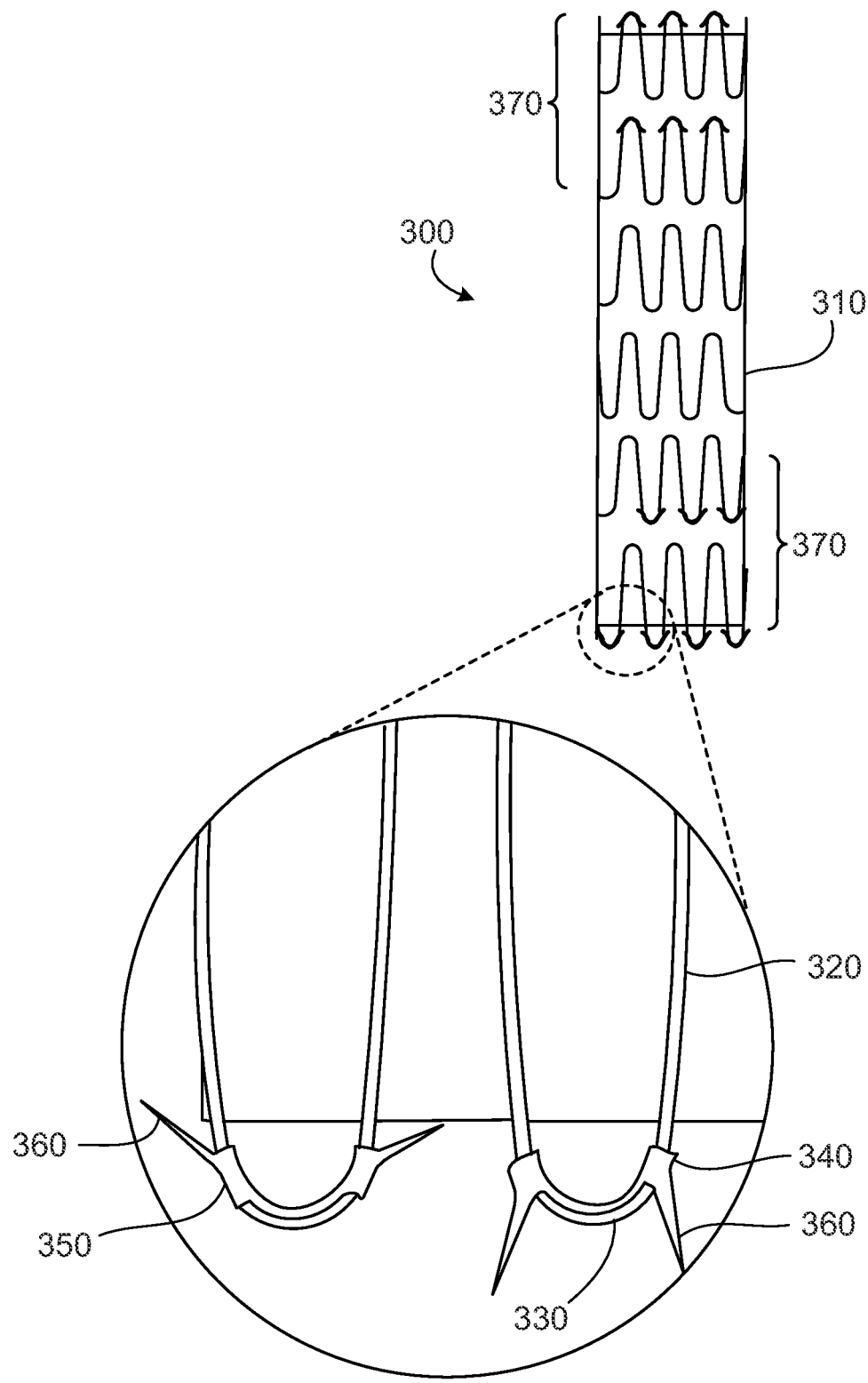
FIG. 3 illustrates another type of implantable medical device including fixation anchors.

FIG. 3 illustrates another type of medical device that includes embodiments of the fixation anchors provided herein. In particular, FIG. 3 depicts an example stent graft device 300. Stent graft devices, in general, can be used as a liner inside a blood vessel to either remedy aneurisms in the wall of the vessel, or to open a conduit in an occluded vessel. The example stent graft device 300 generally includes a membrane 310, frame members 320, and fixation anchors 340/350 located at bend portions 330.

First of all, it can be seen that the tissue engagement members 360 of the fixation anchors 340/350 are orientated differently as compared to the tissue engagement members 230 of the example occluder device 100 described above. That is, whereas the tissue engagement members 230 of FIG. 2, in relation to example occluder device 100, extended within a plane defined by the bent frame members 230, in FIG. 3 the tissue engagement members 360 extend transversely from the plane defined by the bent frame members 320. Both configurations are generally functions of the manner in which the respective device interfaces with the surrounding tissue to which it will be anchored. In the case of the example stent graft device 300, the outer wall of the example stent graft device 300 may be generally parallel to the wall of the blood vessel in which it is placed. Therefore, the desired orientation of the tissue engagement members 360 may be generally transverse from the wall of the example stent graft device 300, so as to engage with the parallel vessel wall.

In some embodiments, the self-expanding nature of the example stent graft device 300 will provide the requisite force to properly engage the tissue engagement members 360 with the surrounding tissue. However, in some embodiments, a supplemental force can be applied—for example from a balloon device—to help attain a proper tissue contact, engagement, or puncture force by the fixation anchors 340/350.

The example stent graft device 300, as shown, can include multiple rows of oscillating frame members 320 that each surround a transverse circumference of the example stent graft device 300. For ease of description, the oscillating frame members 320 can be said to have peaks and valleys—as shown in FIG. 3. That is, each of the multiple bend portions 330 may be considered either a peak or a valley of the oscillating frame members 320. It should be understood that each peak and/or valley is a candidate location for a fixation anchor 340/350 installed thereat, and the fixation anchors provided herein can accommodate such an arrangement. In actual practice, it may be desirable to use fewer locations of fixation anchors 340/350, versus at every peak and valley. Any and all such desired patterns are within the scope of this disclosure. For example, one or more ends of the example stent graft device 300 can include one or more regions known as sealing cuffs 370. In the sealing cuffs 370 portions, a higher density of fixation anchors 340/350 may be desirable in comparison to other regions of the example stent graft device 300. That is, in some embodiments, it may be desirable to fixedly anchor one or both ends of the medical device to the surrounding tissue, while allowing other regions to remain generally free-floating. It should be understood that the fixation anchors provided herein can accommodate all such desired arrangements. For example, on a single row of frame members 320, a fixation anchor 340/350 can be installed on every peak and every valley. As another example, fixation anchors may only be installed on peaks (e.g., every peak, every-other peak, or every third peak) and not on valleys, or only on valleys (e.g., every valley, every-other valley, or every third valley) and not on peaks. Additional examples include a fixation anchor on alternating peaks (e.g., every-other peak) and on alternating valleys (e.g., every-other valley). Any combination and subcombination is envisioned and is within the scope of the fixation anchor disclosure provided herein.

The fixation anchors 340 and 350 are depicted as having tissue engagement members 360 that are oriented in disparate directions with respect to the axis of the example stent graft device 300. That is, fixation anchor 340 has its tissue penetration members 360 extending away from the body of the example stent graft device 300. In contrast, fixation anchor 350 has its tissue penetration members 360 extending towards the body of the example stent graft device 300. Such a disparate combination of the orientation of tissue engagement members 360 can provide an anchoring capability that resists movement of the example stent graft 300 in both axial directions. This exemplifies, as with the capability to place fixation anchors 340/350 at multiple positions, that multiple orientations of the tissue engagement members 360 with respect to the frame members 320 are possible. Such flexibility can facilitate use of the fixation anchors provided herein to attain the particular features that are desired for a particular type of medical device and for the device's context of use.

The orientation of the tissue engagement members 360 can affect the potential for the anchoring/holding strength of the fixation anchors 340/350 as a function of the direction of an applied removal force. That is, an individual tissue engagement member 360 may not provide substantial resistance to removal from the tissue if a force is applied directly opposite to the direction of its insertion to the tissue (with the exception of a barbed tip as described below). In contrast, a far greater anchoring strength can be achieved as against a force that is applied laterally to, or in directional alignment with, the insertion direction. This feature can be strategically used in regard to particular devices, for example, as will now be described in relation to FIG. 4.

Figure 4:
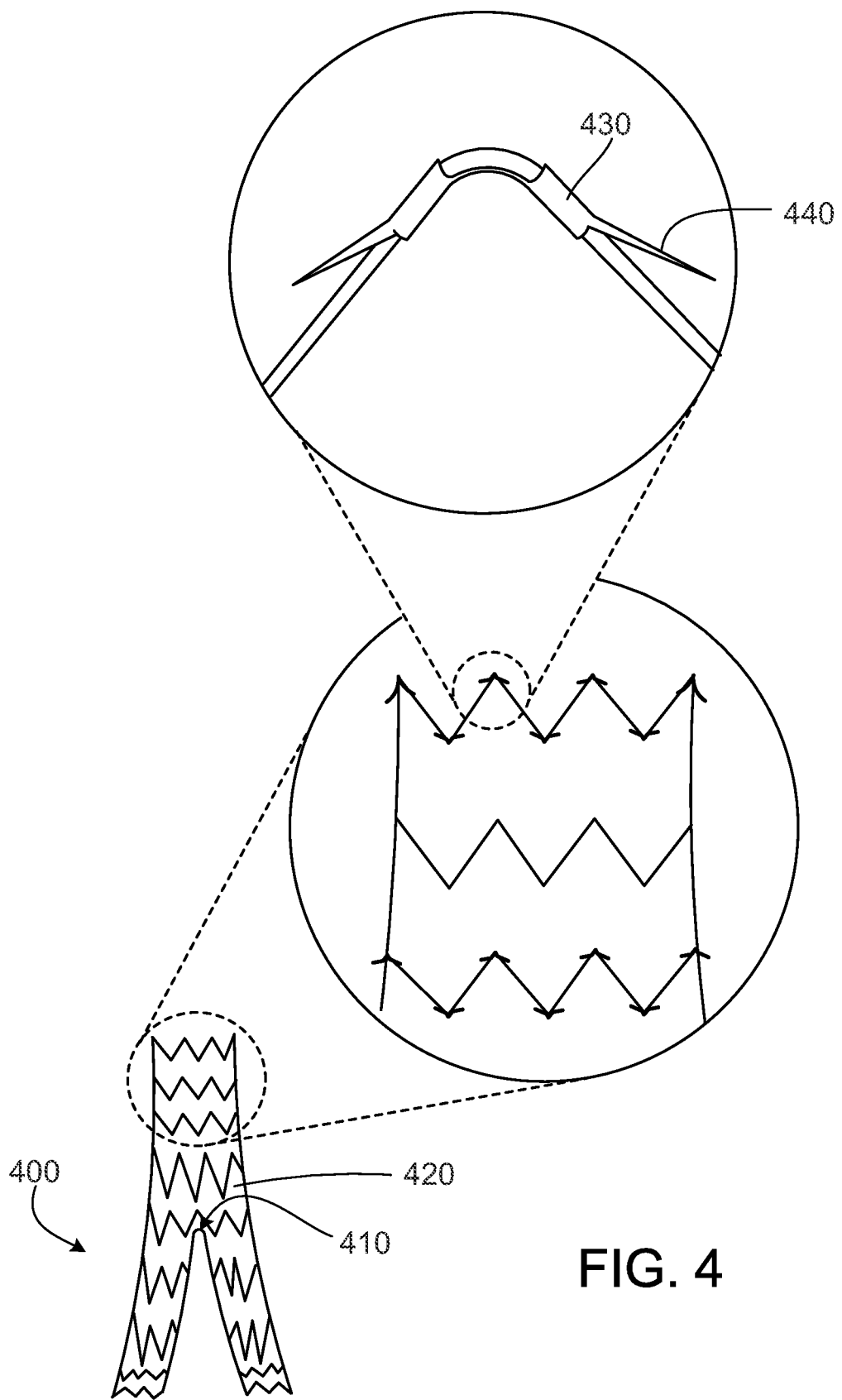
FIG. 4 illustrates another type of implantable medical device including fixation anchors.

FIG. 4 depicts another example embodiment of an implantable medical using an embodiment of the fixation anchors provided herein. In particular, an example AAA stent graft device 400 is illustrated. The AAA stent graft device 400 is a specialized type of a stent graft that shares many functional similarities to the example stent graft 300 described above. However, the AAA stent graft device 400 is specifically designed to be placed within a patient's aorta in their abdominal region. The AAA stent graft device 400 therefore includes a bifurcation 410 that divides the aorta's blood flow as the blood travels from the aorta to enter the left and right femoral arteries. Because of the direction of the blood flow through the AAA stent graft device 400 (downward with respect to FIG. 4), the blood exerts a force on the interior surface of the membrane 420 at the bifurcation 410. That force serves to push the entire AAA stent graft device 400 downward (in the direction of the blood flow). That pushing force can tend to cause the AAA stent graft device 400 to be dislodged from its intended position within the vasculature of the patient.

The orientation of the tissue engagement members 440 of the fixation anchors 430 can be strategically selected in order to counteract the downward blood flow force on the AAA stent graft device 400. As described previously, the highest relative anchoring strength of tissue engagement members 440 can generally be achieved against a force that is applied laterally to, or in directional alignment with, the insertion direction. Therefore, an orientation of the tissue engagement members 440 that results in an insertion direction that is relatively parallel to the blood flow, while also engaging enough aortic wall tissue, may be desirable for counteracting the force exerted by the blood flow on the bifurcation 410. This approximate orientation is depicted in the magnified view of the fixation anchor 430 in FIG. 4.

Figure 5:
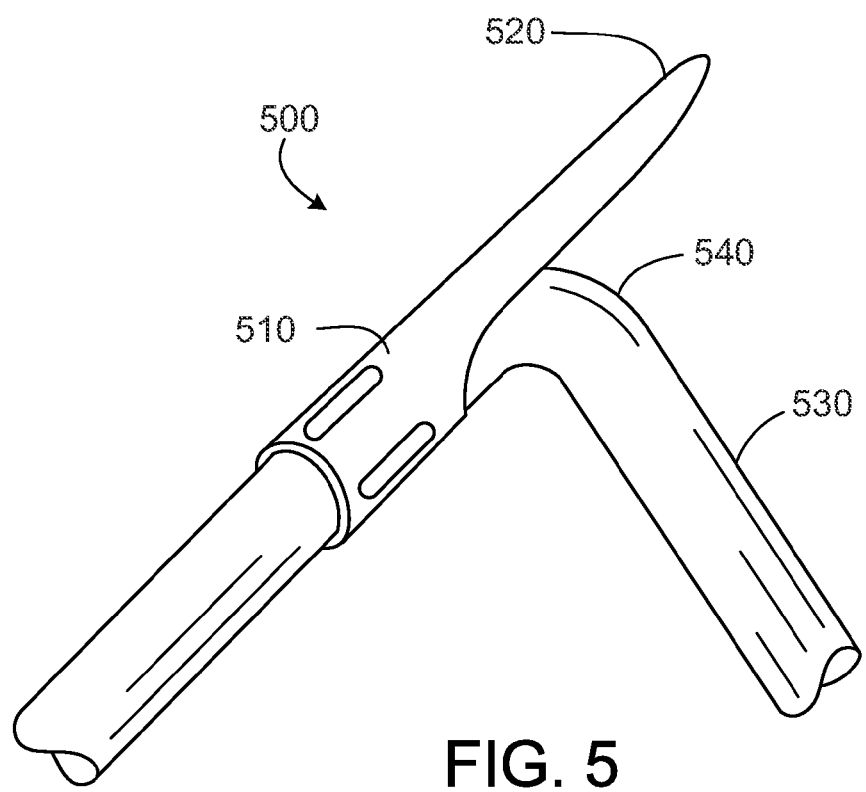
FIG. 5 is a perspective view of an alternative embodiment of a fixation anchor.

FIG. 5 depicts another example embodiment of a fixation anchor 500. This example embodiment includes a single cuff 510. The cuff 510 in this embodiment, and in all other embodiments, can be optionally fixedly attached to frame member 530 by, for example, crimping the cuff 510 to the frame member 530. Crimping is just one of the methods envisioned for fixedly attaching a cuff of a fixation anchor to a frame member. Various other methods, such as welding, gluing, and using an interference fit, are also envisioned. In a single cuff embodiment such as the example fixation anchor 500, the cuff 510 can generally be fixedly attached to the frame member 530 to establish and maintain the desired axial position and radial orientation of the single cuff fixation anchor 500. In contrast, in embodiments of fixation anchors having two cuffs, as described previously, a bend in the frame member, in combination with properties of the fixation anchor itself, can be used to axially position and radially orient the fixation anchor—without having to fixedly attach a cuff to the frame member.

The tissue engagement member 520 of fixation anchor 500 is depicted as being in alignment with the axis of the cuff 510. As will be described further, the orientation of the tissue engagement member 520 in relation to the frame member 530 can have a wide degree of variety in terms of angles, directions, and attachment locations. Further, the tip of the tissue engagement member 520 can have many different designs, as will be described below. Those factors can be strategically customized to compliment the particular medical device on which the fixation anchors are used, and the context in which the device is used.

Figure 6:
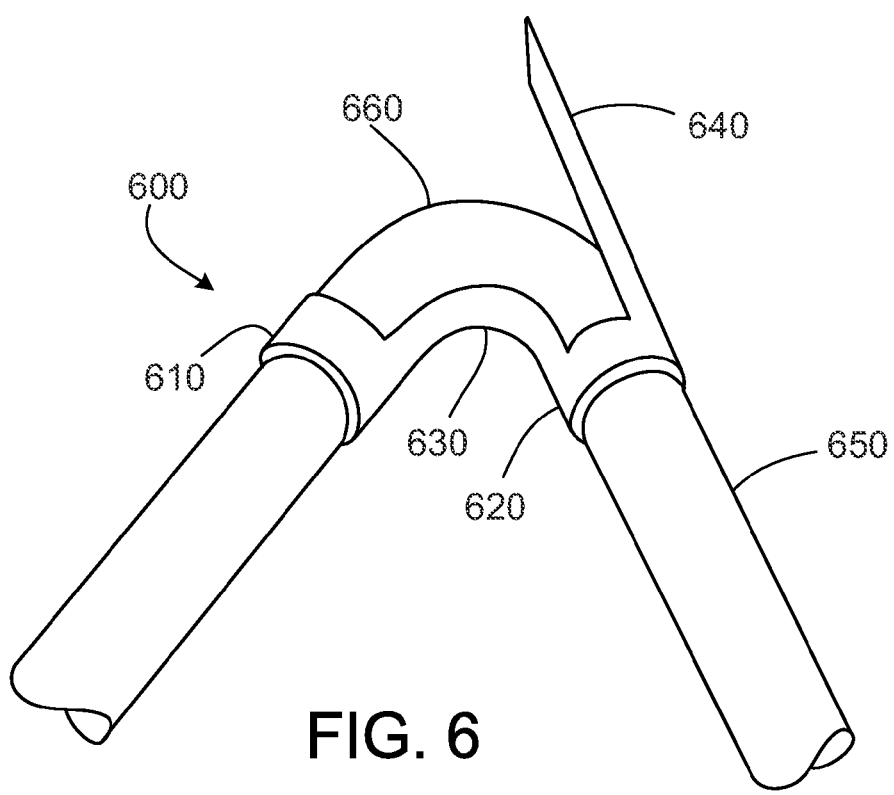
FIG. 6 is a perspective view of an alternative embodiment of a fixation anchor.

FIG. 6 depicts another example embodiment of a fixation anchor 600. This embodiment includes a first cuff 610 and a second cuff 620. The first cuff 610 and the second cuff 620 can be positioned on opposite sides of a bend portion 660 of frame member 650, as shown. The first cuff 610 and second cuff 620 can have a slip fit relation to the frame member 650, or one or both cuffs 610/620 can be fixedly coupled to the frame member 650. The first and second cuffs 610/620 can be conjoined by one or more cuff joining members 630. A tissue engagement member 640 can project from the second cuff 620 generally in the direction away from the frame member 650, or in any other suitable direction. The tissue engagement member 640 can be oriented in alignment with the axis of the second cuff 620 as shown, or alternatively the tissue engagement member 640 can be orientated at any appropriate angle with respect to an axial-datum defined by the second cuff 620.

Figure 7:
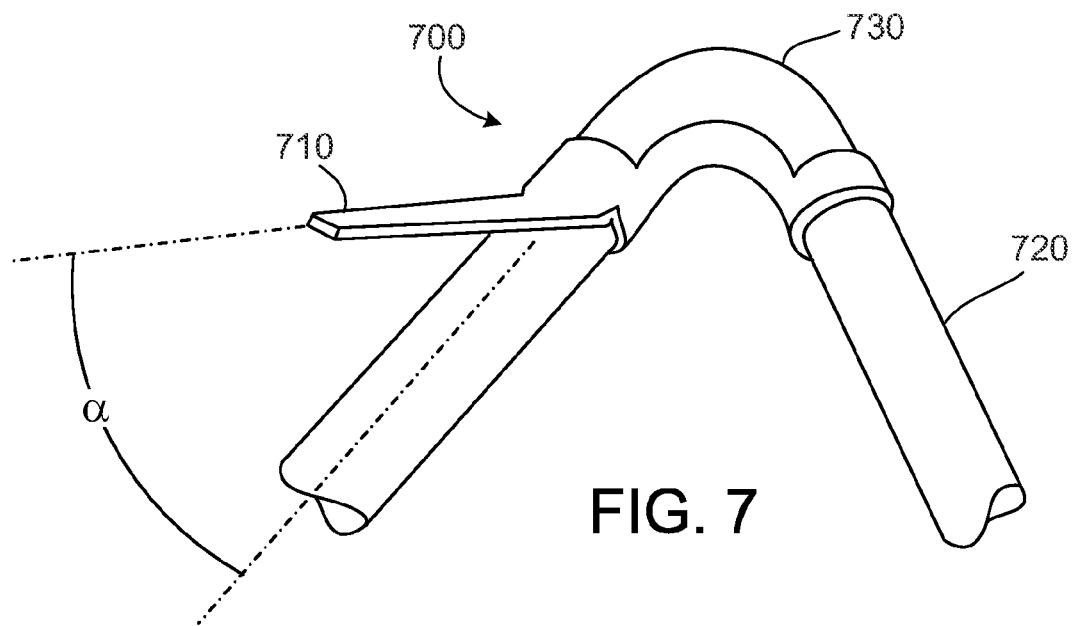
FIG. 7 is a perspective view of an alternative embodiment of a fixation anchor.
Figure 8:
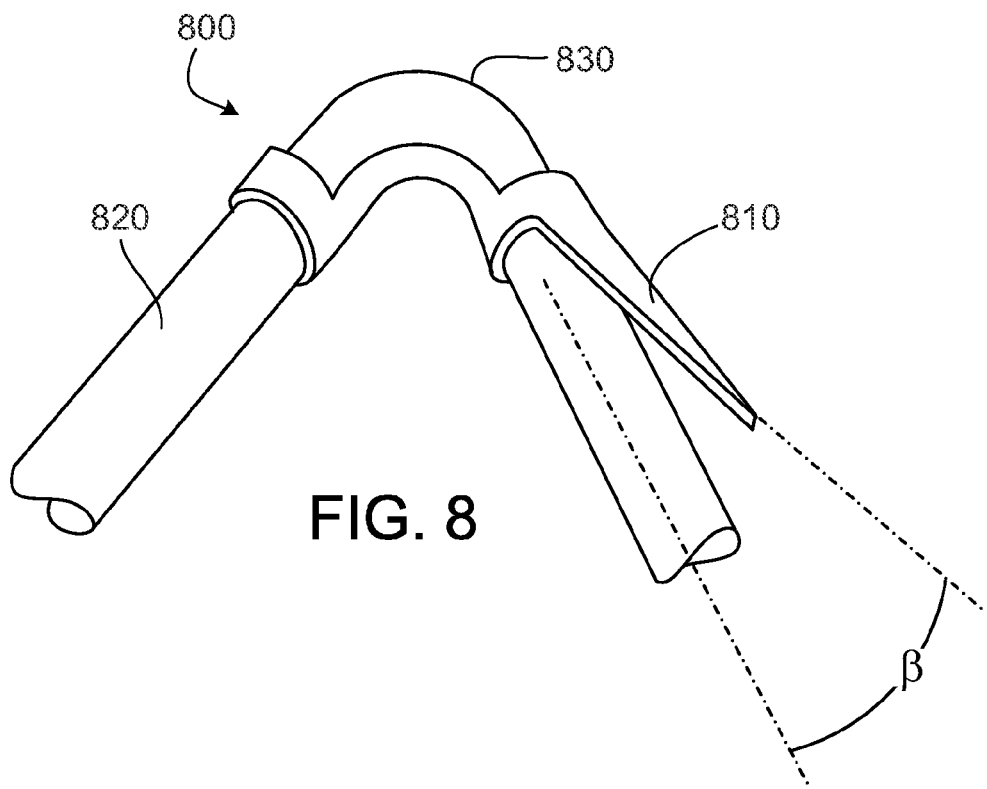
FIG. 8 is a perspective view of an alternative embodiment of a fixation anchor.

FIGS. 7 and 8 depict additional example embodiments of fixation anchors 700 and 800, respectively. These embodiments can be considered to share some similar features with the example fixation anchors 200 and 600 described above, and additionally include certain different aspects regarding the tissue engagement members 710 and 810. For example, the tissue engagement members 710 and 810 can be directed away from the bend portions 730/830, and at angles α and β from the axis of the corresponding frame members 720/820. Angles α and β can range from between 0-180 degrees in some embodiments, between 120-150 degrees in some embodiments, between 0-90 degrees in some embodiments, between 15-75 degrees in some embodiments, between 30-60 degrees in some embodiments, or between 10-45 degrees in some embodiments. Other angles are also possible. In some examples, α and β are the same angle, and in some examples α and β are different angles.

The tissue engagement members 710 and 810 are illustrated as having different styles of tips. In particular, the tip of tissue engagement member 710 is depicted as being blunt, in contrast to the tissue engagement member 810 that is depicted as having a sharply pointed tip. In some implementations when anchoring by tissue penetration is desired, the sharply pointed tip of tissue engagement member 810 may be preferable. By contrast, in implementations where tissue penetration is not desired, the blunt tip of tissue engagement member 710 may be preferable.

FIGS. 9-11 and 13 depict still further example embodiments of fixation anchors 900, 1000, 1100, 1300, and 1400. These embodiments can be considered to share some similar features with the example fixation anchors 200, 600, 700, and 800 described above, with the most notable exception being that the embodiments depicted in FIGS. 9-11 and 13 each include two tissue engagement members. In each example embodiment of fixation anchors 900, 1000, 1100, 1300, and 1400, at least one tissue engagement member projects from each cuff. The differences between the fixation anchors 900, 1000, 1100, 1300, and 1400 reside in the orientations and directions that the tissue engagement members project from the cuffs, and in the different styles of tips of the tissue engagement members.

Figure 9:
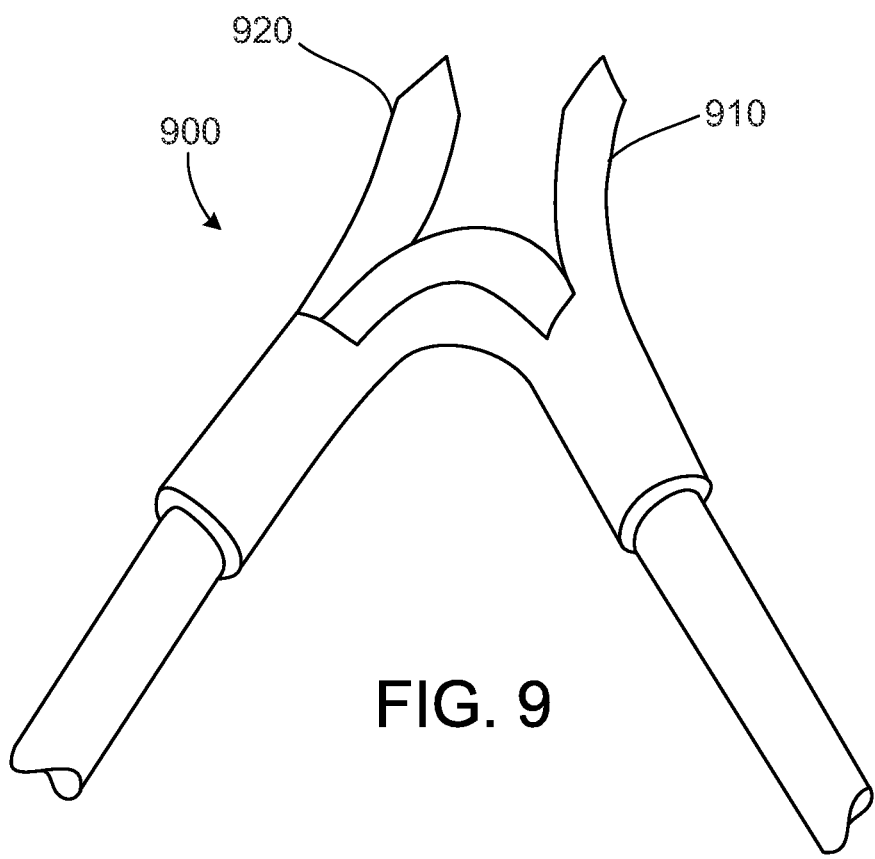
FIG. 9 is a perspective view of an alternative embodiment of a fixation anchor.

For example, the example fixation anchor 900 of FIG. 9 includes two tissue engagement members 910/920 that each project from a different cuff, respectively. The tissue engagement members 910/920 can both project, as shown, generally away from their host frame member.

Figure 10:
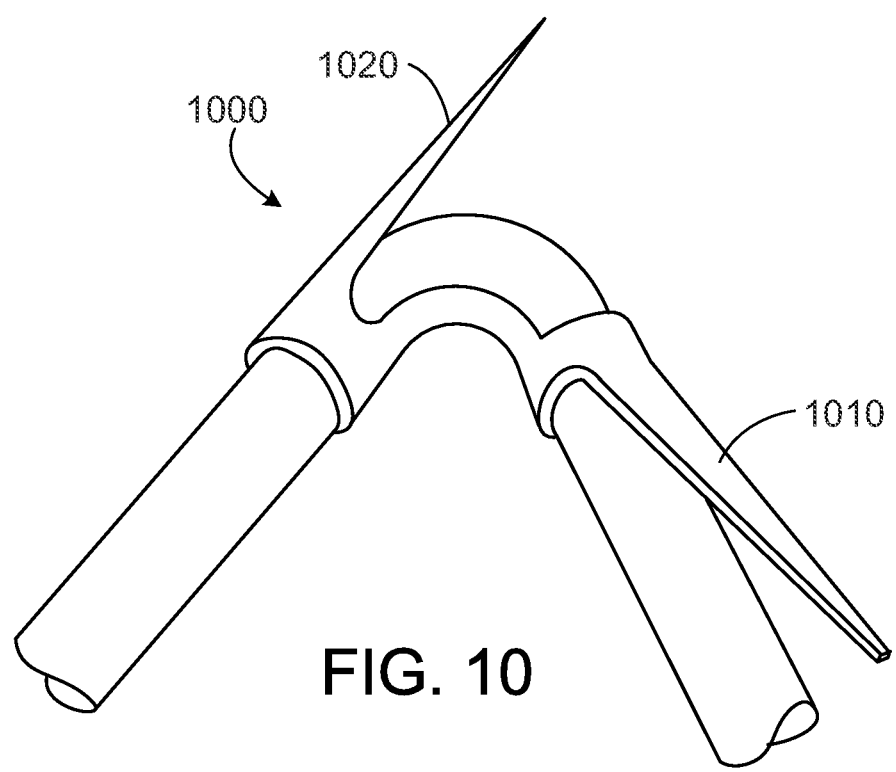
FIG. 10 is a perspective view of an alternative embodiment of a fixation anchor.

The example fixation anchor 1000 of FIG. 10 similarly includes two tissue engagement members 1010/1020. However, rather than pointing in the same general direction, the two tissue engagement members 1010/1020 point in dissimilar directions, i.e. tissue engagement member 1010 points towards the host frame member, while tissue engagement member 1020 points away from the respective host frame member.

Figure 11:
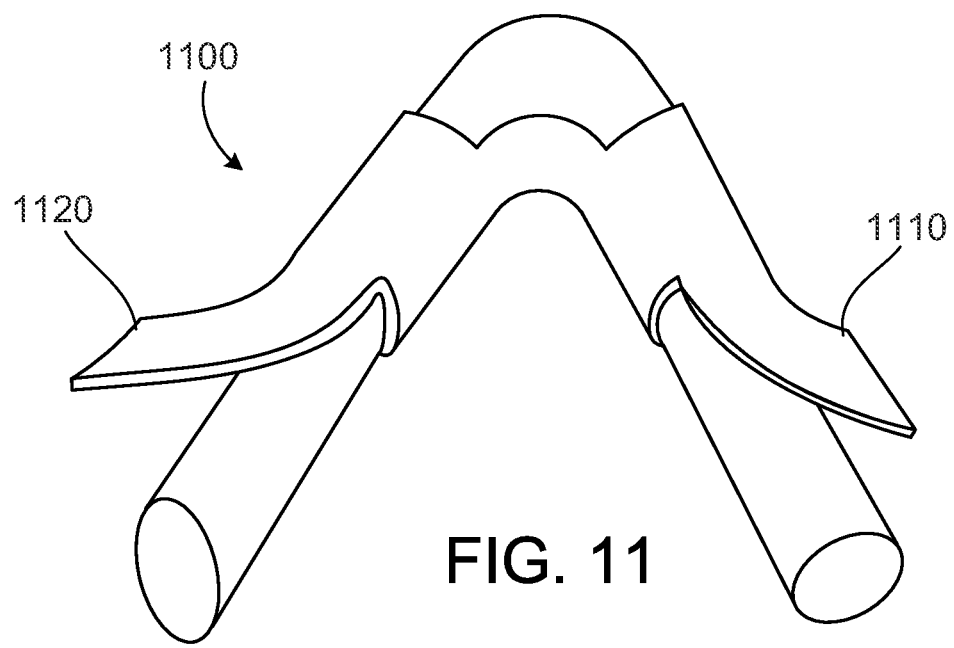
FIG. 11 is a perspective view of an alternative embodiment of a fixation anchor.

The example fixation anchor 1100 of FIG. 11 also includes two tissue engagement members 1110/1120. In this embodiment, the two tissue engagement members 1110/1120 both project generally in the direction of the host frame member.

Figure 13:
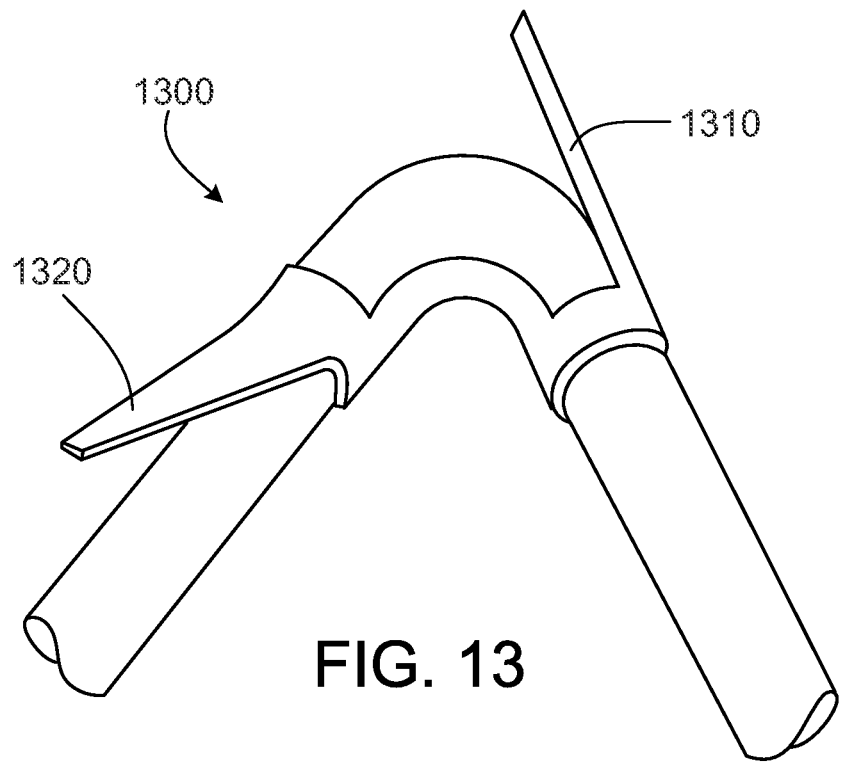
FIG. 13 is a perspective view of an alternative embodiment of a fixation anchor.

The example fixation anchor 1300 of FIG. 13 also includes two tissue engagement members 1310/1320. However, rather than pointing in the same general direction, the two tissue engagement members 1310/1320 point in dissimilar directions.

Figure 12:
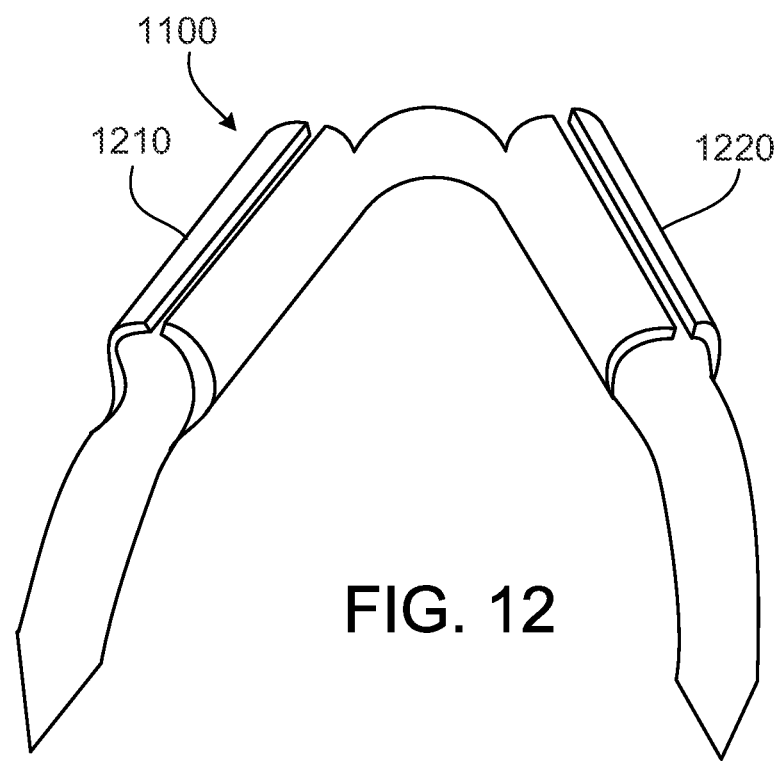
FIG. 12 is a perspective view of an alternative embodiment of a fixation anchor.

FIG. 12 depicts a bottom view of the example fixation anchor 1100. A first cuff 1210 and a second cuff 1220 are shown. Each cuff 1210/1220 has a linear gap through the wall of the cuff in an axial direction. These cuts in the cuffs 1210/1220 can be used to efficiently install the fixation anchor 1100 onto a host frame member. For example, by virtue of being cut or split, the tubular walls of the cuffs 1210/1220 can be elastically deflected to open the tubular walls into a U-shaped cross-section. The cuffs 1210/1220 can then be placed onto the host frame members, and allowed to return to their undeflected configuration (to surround/engage the frame members). This process of assembling the cuffs 1210/1220 onto the frame members can provide for an efficient assembly process.

Figure 14:
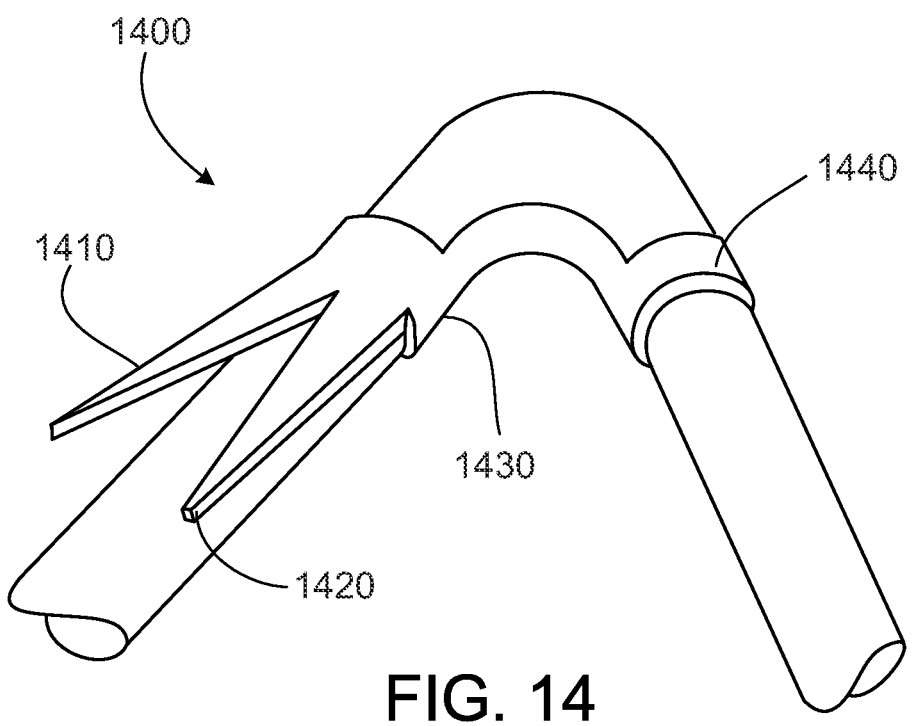
FIG. 14 is a perspective view of an alternative embodiment of a fixation anchor.

FIG. 14 depicts yet another example embodiment of a fixation anchor 1400. This embodiment illustrates that an individual cuff 1430 can have multiple (e.g., two or more) tissue engagement members 1410/1420 projecting from it. In fact, an individual cuff could have three or more tissue engagement members projecting from it. The multiple tissue engagement members 1410/1420 can project from the corresponding cuff 1430 in a similar direction (as shown), or in dissimilar directions (not shown), and at similar or dissimilar angles with respect to the axis of the frame members. Further, both cuffs 1430/1440 can have multiple tissue engagement members projecting from them. Still further, the tissue engagement members 1410/1420 can have different tip configurations. By combining such design variables, a large number of permutations of fixation anchor designs are possible.

A variety of example tip configurations for the tissue engagement members are illustrated in FIGS. 15A-15E. As described previously, in some implementations, a tissue engagement member configured to penetrate tissue may be desired. In other implementations, a tissue engagement member with a blunt tip that is configured to make contact with the tissue but not penetrate the tissue may be desired. Still further types of special tip configurations are also envisioned. A single medical device may strategically use a combination of various types of tip configurations for the device's fixation anchor tissue engagement members, in some implementations.

Figure 15A:
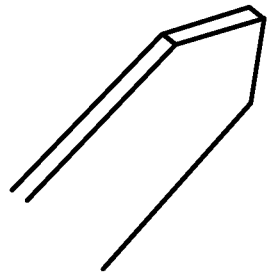
FIGS. 15A-15E illustrate a variety of embodiments of tissue engagement tips for fixation anchors.

FIG. 15A illustrates a type of a tissue engagement tip that may be intended to penetrate surrounding tissue. The edges of the tip may also be sharpened to facilitate penetration. Whereas, in the illustrated embodiment, the apex of the tip is approximately on the centerline of the tip, in other embodiments, the apex of the tip may be in alignment with an edge of the tissue engagement member. In some fixation anchor implementations, it can be desired to be able to relatively atraumatically remove the tissue engagement members from a penetrated tissue to reposition or remove the medical device. The embodiment shown may facilitate relatively convenient removal of the tip from tissue after it has penetrated the tissue, for example, because the tip does not include a barb.

Figure 15B:
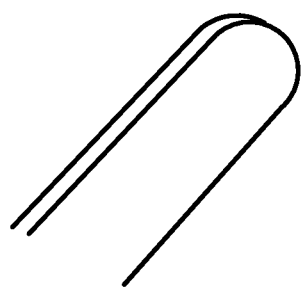

FIG. 15B illustrates a type of a tissue engagement tip provides a blunt tip that may contact tissue but may avoid penetrating the tissue. In some implementations, it may be desirable to provide some anchoring strength without piercing the surrounding tissue. A blunt tip as shown may enable such an implementation. Tips with additional surface area at a tissue contact region (e.g., a "paddle" shape or a "shoe" shape) can also be used.

Figure 15C:
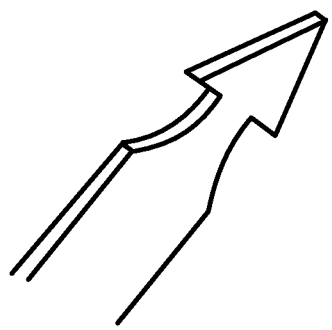
Figure 15D:
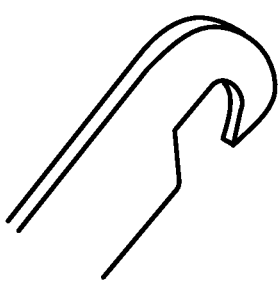

FIGS. 15C and 15D illustrate types of tissue engagement tips that may be intended to penetrate tissue, and to provide a substantial anchoring strength—even in the direction linearly opposite to the penetration direction. These tip embodiments therefore include one or more barbed portions. As a result, when a tissue engagement member with this type of tip has penetrated tissue, the barbed portions may tend to resist removal because the edges of the barbed portions will make contact with internal tissue so that the tissue will interfere with the tip's removal. Many other styles of barbed tip embodiments are also envisioned.

Figure 15E:
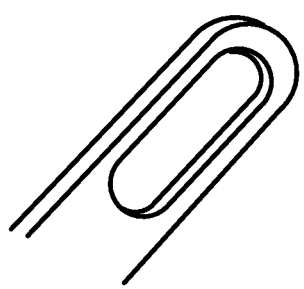

FIG. 15E illustrates a type of tissue engagement tip that may be intended to allow for tissue ingrowth to thereby supplement the anchoring strength of the tissue engagement member. This embodiment can include, for example, an eyelet, as shown, to encourage or facilitate the natural response of tissue to grow and engage the tissue engagement member. An eyelet in the tip is just one of many types of tips that are envisioned that can encourage tissue ingrowth, to provide supplemental anchoring strength.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims. For example, the actions recited in the claims can be performed in a different order and still achieve desirable results.

What is claimed is:

1. An implantable medical device, comprising:
   a frame comprising at least one elongate member; and
   a fixation member comprising a first cuff, a second cuff, at least a first tissue engagement member configured to anchor to tissue at an implant site to thereby hold the implantable medical device in a position at the implant site, and a cuff joining member comprising an arcuate shape and connected at a first end to the first cuff and at a second end to the second cuff;
   wherein the first cuff substantially surrounds a perimeter of a first portion of the at least one elongate member, the second cuff substantially surrounds a perimeter of a second portion of the at least one elongate member, and the cuff joining member does not substantially surround a perimeter of any portion of the at least one elongate member,
   and wherein the first and second cuffs each have a slip-fit relation with the at least one elongate member to allow for relative movement between the fixation member and the at least one elongate member in response to a bending of the at least one elongate member.

2. The implantable medical device of claim 1, wherein the at least a first tissue engagement member is configured to penetrate the tissue at the implant site.

3. The implantable medical device of claim 1, wherein the at least a first tissue engagement member is configured to contact, without penetrating, the tissue at the implant site.

4. The implantable medical device of claim 1, wherein the at least a first tissue engagement member extends from the first cuff.

5. The implantable medical device of claim 4, further comprising a second tissue engagement member that extends from the second cuff.

6. The implantable medical device of claim 5, wherein the at least a first tissue engagement member extends towards the frame of the implantable medical device, and wherein the second tissue engagement member extends away from the frame of the implantable medical device.

7. The implantable medical device of claim 5, wherein the at least a first tissue engagement member extends towards the frame of the implantable medical device, and wherein the second tissue engagement member extends towards the frame of the implantable medical device.

8. The implantable medical device of claim 5, wherein the at least a first tissue engagement member extends away from the frame of the implantable medical device, and wherein the second tissue engagement member extends away from the frame of the implantable medical device.

9. The implantable medical device of claim 1, wherein the at least a first tissue engagement member extends from the second cuff.

10. The implantable medical device of claim 1, wherein the fixation member further comprises a second tissue engagement member, and wherein the at least a first and the second tissue engagement members each extend from the first cuff.

11. The implantable medical device of claim 10, wherein the at least a first and the second tissue engagement members each extend towards the frame of the implantable medical device.

12. The implantable medical device of claim 1, wherein the first cuff and the second cuff are respectively positioned on opposite sides of a bend portion of the at least one elongate member.

13. The implantable medical device of claim 12, wherein the cuff joining member is configured to seek a position at an inside curvature of the bend portion of the at least one elongate member in response to the bending of the at least one elongate member.

14. The implantable medical device of claim 1, wherein the first cuff defines a first lumen through the first cuff, the second cuff defines a second lumen through the second cuff, and wherein a first axis coincident with the first lumen is not collinear with a second axis coincident with the second lumen.

15. The implantable medical device of claim 14, wherein the first axis and the second axis intersect at an angle in the range of 10-80 degrees.

16. The implantable medical device of claim 15, wherein the first axis and the second axis intersect at an angle in the range of 20-70 degrees.

17. The implantable medical device of claim 14, wherein the first axis and the second axis intersect at an angle in the range of 30-60 degrees.

18. The implantable medical device of claim 1, wherein the at least one elongate member comprises a wire.

19. The implantable medical device of claim 1, wherein the wire comprises nitinol.

20. The implantable medical device of claim 1, wherein the fixation member comprises a nitinol tube from which the first cuff, the second cuff, the cuff joining member, and the tissue engagement member are formed.

21. The implantable medical device of claim 1, wherein the first cuff includes a generally linear gap along an axial direction of a wall of the first cuff.

22. The implantable medical device of claim 1, wherein the first cuff completely surrounds the perimeter of the first portion of the at least one elongate member.

23. An implantable medical device, comprising:
   a frame comprising at least one elongate member; and
   a fixation member comprising a first cuff, a second cuff, a tissue engagement member configured to anchor to tissue at an implant site to thereby hold the implantable medical device in a position at the implant site, and an elongate joining member comprising a proximal end and a distal end, the elongate joining member connected at the proximal end to the first cuff and at the distal end to the second cuff, the elongate joining member further defining an arcuate shape between the proximal end and the distal end;
   wherein the first cuff substantially surrounds a perimeter of a first portion of the at least one elongate member, the second cuff substantially surrounds a perimeter of a second portion of the at least one elongate member, and the elongate joining member does not substantially surround a perimeter of any portion of the at least one elongate member,
   and wherein the first and second cuffs have a slip-fit relation with the at least one elongate member to allow for relative movement between the fixation member and the at least one elongate member in response to a bending of the at least one elongate member.

24. An implantable medical device, comprising:
a frame comprising at least one elongate member; and
a fixation member comprising a first tubular member, a second tubular member, a tissue engagement member configured to anchor to tissue at an implant site to thereby hold the implantable medical device in a position at the implant site, and an elongate joining member comprising a proximal end and a distal end, the elongate joining member connected at the proximal end to the first tubular member and at the distal end to the second tubular member, the elongate joining member further defining an arcuate shape between the proximal end and the distal end;
wherein the first tubular member substantially circumferentially surrounds a first portion of the at least one elongate member, the second tubular member substantially circumferentially surrounds a second portion of the at least one elongate member, and the elongate joining member does not substantially circumferentially surround any portion of the at least one elongate member,
and wherein the first and second tubular members have a slip-fit relation with the at least one elongate member to allow for relative movement between the fixation member and the at least one elongate member in response to a bending of the at least one elongate member.

* * * * *